(12) United States Patent
Patel

(10) Patent No.: US 9,872,686 B2
(45) Date of Patent: *Jan. 23, 2018

(54) SURGICAL FASTENING APPARATUS

(71) Applicant: Covidien LP, Mansfield, MA (US)

(72) Inventor: Nihir Patel, Stamford, CT (US)

(73) Assignee: Covidien LP, Mansfield, MA (US)

( * ) Notice: Subject to any disclaimer, the term of this patent is extended or adjusted under 35 U.S.C. 154(b) by 25 days.

This patent is subject to a terminal disclaimer.

(21) Appl. No.: 15/205,244

(22) Filed: Jul. 8, 2016

(65) Prior Publication Data

US 2016/0317153 A1 Nov. 3, 2016

Related U.S. Application Data

(63) Continuation of application No. 13/787,368, filed on Mar. 6, 2013, now Pat. No. 9,408,603, which is a
(Continued)

(51) Int. Cl.
A61B 17/072 (2006.01)
A61B 17/115 (2006.01)
A61B 17/068 (2006.01)
A61B 17/064 (2006.01)
A61B 17/11 (2006.01)
(Continued)

(52) U.S. Cl.
CPC ........ *A61B 17/1155* (2013.01); *A61B 17/068* (2013.01); *A61B 17/072* (2013.01); *A61B 17/07207* (2013.01); *A61B 17/07292* (2013.01); *A61B 17/11* (2013.01); *A61B 17/115* (2013.01); *A61B 17/0643* (2013.01); *A61B 17/1114* (2013.01); *A61B 17/32053* (2013.01); *A61B 2017/07214* (2013.01); *A61B 2090/037* (2016.02)

(58) Field of Classification Search
CPC . A61B 17/068; A61B 17/0686; A61B 17/072; A61B 17/07207; A61B 17/07292; A61B 17/115; A61B 17/1155; A61B 17/0644; A61B 2017/07214
USPC .............. 227/19, 175.1, 175.2, 176.1, 180.1; 606/139, 143, 153, 219
See application file for complete search history.

(56) References Cited

U.S. PATENT DOCUMENTS

| 1,480,746 A | 1/1924 | DeBie |
| 3,232,089 A | 2/1966 | Samuels et al. |

(Continued)

FOREIGN PATENT DOCUMENTS

| EP | 384647 A1 | 8/1990 |
| EP | 594004 A1 | 4/1994 |

(Continued)

OTHER PUBLICATIONS

Canadian Office Action issued in corresponding Canadian Appln. No. 2,718,156 dated May 27, 2016.

*Primary Examiner* — Scott A. Smith

(57) ABSTRACT

A surgical fastening apparatus includes a fastener retaining frame having a first annular portion having a plurality of retainers circumferentially disposed thereon and a second annular portion having a plurality of circumferentially arranged perforations. The fastener retaining frame is detachably secured to a supporting structure. After the plurality of surgical fasteners has been mated with the plurality of retainers, an annular blade severs the perforations.

23 Claims, 6 Drawing Sheets

Related U.S. Application Data continuation of application No. 12/899,617, filed on Oct. 7, 2010, now Pat. No. 8,413,872.

(60) Provisional application No. 61/326,292, filed on Apr. 21, 2010, provisional application No. 61/255,529, filed on Oct. 28, 2009.

(51) Int. Cl.
*A61B 17/3205* (2006.01)
*A61B 90/00* (2016.01)

(56) References Cited

U.S. PATENT DOCUMENTS

| | | |
|---|---|---|
| 3,254,650 A | 6/1966 | Collito |
| 3,258,012 A | 6/1966 | Nakayama et al. |
| 3,366,301 A | 1/1968 | Mallina |
| 3,494,533 A | 2/1970 | Green et al. |
| 3,496,939 A | 2/1970 | Odiaga et al. |
| 3,519,187 A | 7/1970 | Kapitanov et al. |
| 3,771,526 A | 11/1973 | Rudie |
| 3,974,835 A | 8/1976 | Hardy, Jr. |
| 4,055,186 A | 10/1977 | Leveen |
| 4,166,466 A | 9/1979 | Jarvik |
| 4,182,339 A | 1/1980 | Hardy, Jr. |
| 4,198,982 A | 4/1980 | Fortner et al. |
| 4,233,981 A | 11/1980 | Schomacher |
| 4,304,236 A | 12/1981 | Conta et al. |
| 4,350,160 A | 9/1982 | Kolesov et al. |
| 4,351,466 A | 9/1982 | Noiles |
| 4,356,601 A | 11/1982 | Kimura |
| 4,368,736 A | 1/1983 | Kaster |
| 4,423,730 A | 1/1984 | Gabbay |
| 4,467,804 A | 8/1984 | Hardy et al. |
| 4,473,077 A | 9/1984 | Noiles et al. |
| 4,476,863 A | 10/1984 | Kanshin et al. |
| D276,650 S | 12/1984 | Green et al. |
| 4,488,523 A | 12/1984 | Shichman |
| 4,505,272 A | 3/1985 | Utyamyshev et al. |
| 4,508,374 A | 4/1985 | Kantor |
| 4,534,088 A | 8/1985 | Ricke |
| 4,552,148 A | 11/1985 | Hardy, Jr. et al. |
| 4,705,039 A | 11/1987 | Sakaguchi et al. |
| 4,708,141 A | 11/1987 | Inoue et al. |
| 4,752,024 A | 6/1988 | Green et al. |
| 4,766,898 A | 8/1988 | Hardy et al. |
| 4,872,874 A | 10/1989 | Taheri |
| 4,889,119 A | 12/1989 | Jamiolkowski et al. |
| 4,893,622 A | 1/1990 | Green et al. |
| 4,899,744 A | 2/1990 | Fujitsuka et al. |
| 4,903,697 A | 2/1990 | Resnick et al. |
| 4,907,591 A | 3/1990 | Vasconcellos et al. |
| 4,917,114 A | 4/1990 | Green et al. |
| 4,930,674 A | 6/1990 | Barak |
| 4,931,057 A | 6/1990 | Cummings et al. |
| 4,957,499 A | 9/1990 | Lipatov et al. |
| 4,979,954 A | 12/1990 | Gwathmey et al. |
| 5,025,779 A | 6/1991 | Bugge |
| 5,141,516 A | 8/1992 | Detweiler et al. |
| 5,188,638 A | 2/1993 | Tzakis |
| 5,205,459 A | 4/1993 | Brinkerhoff et al. |
| 5,211,649 A | 5/1993 | Kohler et al. |
| 5,222,963 A | 6/1993 | Brinkerhoff et al. |
| 5,234,447 A | 8/1993 | Kaster et al. |
| 5,234,448 A | 8/1993 | Wholey et al. |
| 5,250,058 A | 10/1993 | Miller et al. |
| 5,271,543 A | 12/1993 | Grant et al. |
| 5,282,810 A | 2/1994 | Allen et al. |
| 5,314,436 A | 5/1994 | Wilk |
| 5,346,501 A | 9/1994 | Regula et al. |
| 5,354,304 A | 10/1994 | Allen et al. |
| 5,366,458 A | 11/1994 | Korthoff et al. |
| 5,366,462 A | 11/1994 | Kaster et al. |
| 5,403,333 A | 4/1995 | Kaster et al. |
| 5,403,338 A | 4/1995 | Milo |
| 5,411,508 A | 5/1995 | Bessler et al. |
| 5,425,738 A | 6/1995 | Gustafson et al. |
| 5,425,739 A | 6/1995 | Jessen |
| 5,431,668 A | 7/1995 | Burbank, III et al. |
| 5,437,684 A | 8/1995 | Calabrese et al. |
| 5,443,198 A | 8/1995 | Viola et al. |
| 5,452,733 A | 9/1995 | Sterman et al. |
| 5,474,732 A | 12/1995 | Korthoff et al. |
| 5,486,187 A | 1/1996 | Schenck |
| 5,503,635 A | 4/1996 | Sauer et al. |
| 5,527,324 A | 6/1996 | Krantz et al. |
| 5,562,690 A | 10/1996 | Green et al. |
| 5,639,008 A | 6/1997 | Gallagher et al. |
| 5,649,937 A | 7/1997 | Bito et al. |
| 5,658,300 A | 8/1997 | Bito et al. |
| 5,669,918 A | 9/1997 | Balazs et al. |
| 5,695,504 A | 12/1997 | Gifford, III et al. |
| 5,697,943 A | 12/1997 | Sauer et al. |
| 5,702,412 A | 12/1997 | Popov et al. |
| 5,707,380 A | 1/1998 | Hinchliffe et al. |
| 5,709,335 A | 1/1998 | Heck |
| 5,725,537 A | 3/1998 | Green et al. |
| 5,732,872 A | 3/1998 | Bolduc et al. |
| 5,758,814 A | 6/1998 | Gallagher et al. |
| 5,779,718 A | 7/1998 | Green et al. |
| 5,797,931 A | 8/1998 | Bito et al. |
| 5,797,934 A | 8/1998 | Rygaard |
| 5,817,113 A | 10/1998 | Gifford, III et al. |
| 5,823,956 A | 10/1998 | Roth et al. |
| 5,827,316 A | 10/1998 | Young et al. |
| 5,833,698 A | 11/1998 | Hinchliffe et al. |
| 5,839,639 A | 11/1998 | Sauer et al. |
| 5,855,614 A | 1/1999 | Stevens et al. |
| 5,860,581 A | 1/1999 | Robertson et al. |
| 5,881,943 A | 3/1999 | Heck |
| 5,891,160 A | 4/1999 | Williamson, IV et al. |
| 5,904,697 A | 5/1999 | Gifford, III et al. |
| 5,906,625 A | 5/1999 | Bito et al. |
| 5,916,226 A | 6/1999 | Tozzi |
| 5,944,730 A | 8/1999 | Nobles et al. |
| 5,947,363 A | 9/1999 | Bolduc et al. |
| 5,951,576 A | 9/1999 | Wakabayashi |
| 5,957,363 A | 9/1999 | Heck |
| 5,957,879 A | 9/1999 | Roberts et al. |
| 5,961,481 A | 10/1999 | Sterman et al. |
| 5,964,782 A | 10/1999 | Lafontaine et al. |
| 5,971,973 A | 10/1999 | Peters |
| 5,972,030 A | 10/1999 | Garrison et al. |
| 5,976,159 A | 11/1999 | Bolduc et al. |
| 5,993,468 A | 11/1999 | Rygaard |
| 6,015,416 A | 1/2000 | Stefanchik et al. |
| 6,024,748 A | 2/2000 | Manzo et al. |
| 6,030,395 A | 2/2000 | Nash et al. |
| 6,036,705 A | 3/2000 | Nash et al. |
| 6,056,762 A | 5/2000 | Nash et al. |
| 6,066,144 A | 5/2000 | Wolf et al. |
| 6,080,173 A | 6/2000 | Williamson, IV et al. |
| 6,083,234 A | 7/2000 | Nicholas et al. |
| 6,110,187 A | 8/2000 | Donlon |
| 6,171,319 B1 | 1/2001 | Nobles et al. |
| 6,171,321 B1 | 1/2001 | Gifford, III et al. |
| 6,176,413 B1 | 1/2001 | Heck et al. |
| 6,176,864 B1 | 1/2001 | Chapman |
| 6,183,486 B1 | 2/2001 | Snow et al. |
| 6,187,019 B1 | 2/2001 | Stefanchik et al. |
| 6,187,020 B1 | 2/2001 | Zegdi et al. |
| 6,187,022 B1 | 2/2001 | Alexander, Jr. et al. |
| 6,190,397 B1 | 2/2001 | Spence et al. |
| 6,190,590 B1 | 2/2001 | Randall et al. |
| 6,193,129 B1 | 2/2001 | Bittner et al. |
| 6,193,734 B1 | 2/2001 | Bolduc et al. |
| 6,197,042 B1 | 3/2001 | Ginn et al. |
| 6,206,913 B1 | 3/2001 | Yencho et al. |
| 6,231,506 B1 | 5/2001 | Hu et al. |
| 6,234,995 B1 | 5/2001 | Peacock, III |
| 6,241,741 B1 | 6/2001 | Duhaylongsod et al. |
| 6,241,742 B1 | 6/2001 | Spence et al. |
| 6,241,743 B1 | 6/2001 | Levin et al. |
| 6,248,117 B1 | 6/2001 | Blatter |

(56) References Cited

U.S. PATENT DOCUMENTS

| | | |
|---|---|---|
| 6,253,984 B1 | 7/2001 | Heck et al. |
| 6,254,615 B1 | 7/2001 | Bolduc et al. |
| 6,254,617 B1 | 7/2001 | Spence et al. |
| 6,280,460 B1 | 8/2001 | Bolduc et al. |
| 6,332,468 B1 | 12/2001 | Benetti |
| 6,338,712 B2 | 1/2002 | Spence et al. |
| 6,346,074 B1 | 2/2002 | Roth |
| 6,350,252 B2 | 2/2002 | Ray et al. |
| 6,361,543 B1 | 3/2002 | Chin |
| 6,371,965 B2 | 4/2002 | Gifford, III et al. |
| 6,387,105 B1 | 5/2002 | Gifford, III et al. |
| 6,391,039 B1 | 5/2002 | Nicholas et al. |
| 6,401,721 B1 | 6/2002 | Maginot |
| 6,440,146 B2 | 8/2002 | Nicholas et al. |
| 6,443,965 B1 | 9/2002 | Gifford, III et al. |
| 6,450,390 B2 | 9/2002 | Heck et al. |
| 6,451,034 B1 | 9/2002 | Gifford, III et al. |
| 6,461,365 B2 | 10/2002 | Bolduc et al. |
| 6,471,713 B1 | 10/2002 | Vargas et al. |
| 6,503,259 B2 | 1/2003 | Huxel et al. |
| 6,562,037 B2 | 5/2003 | Paton et al. |
| 6,666,873 B1 | 12/2003 | Cassell |
| 6,726,697 B2 | 4/2004 | Nicholas et al. |
| 6,769,594 B2 | 8/2004 | Orban, III |
| 7,059,510 B2 | 6/2006 | Orban, III |
| 7,168,604 B2 | 1/2007 | Milliman et al. |
| 7,169,158 B2 | 1/2007 | Sniffin et al. |
| 7,204,843 B2 | 4/2007 | Milliman et al. |
| 7,220,237 B2 | 5/2007 | Gannoe et al. |
| 7,223,273 B2 | 5/2007 | Manzo |
| 7,229,428 B2 | 6/2007 | Gannoe et al. |
| 7,303,106 B2 | 12/2007 | Milliman et al. |
| 7,322,994 B2 | 1/2008 | Nicholas et al. |
| 7,338,505 B2 | 3/2008 | Belson |
| 7,438,718 B2 | 10/2008 | Milliman et al. |
| 7,547,312 B2 | 6/2009 | Bauman et al. |
| 7,665,647 B2 | 2/2010 | Shelton, IV et al. |
| 7,669,747 B2 * | 3/2010 | Weisenburgh, II .. A61B 17/105 227/175.1 |
| 7,744,627 B2 * | 6/2010 | Orban, III ............ A61B 17/115 227/175.1 |
| 8,034,064 B2 | 10/2011 | Blatter |
| 8,123,766 B2 | 2/2012 | Bauman et al. |
| 8,181,838 B2 | 5/2012 | Milliman et al. |
| 8,205,782 B2 | 6/2012 | Harari et al. |
| 8,413,872 B2 | 4/2013 | Patel |
| 9,408,603 B2 | 8/2016 | Patel |
| 9,421,013 B2 * | 8/2016 | Patel .................... A61B 17/115 |
| 2003/0183671 A1 * | 10/2003 | Mooradian .......... A61B 17/115 227/175.1 |
| 2008/0058865 A1 | 3/2008 | Wilk |
| 2008/0114385 A1 | 5/2008 | Byrum et al. |
| 2009/0001121 A1 * | 1/2009 | Hess .................... A61B 17/064 227/175.1 |
| 2010/0089971 A1 | 4/2010 | Milliman et al. |
| 2010/0282813 A1 * | 11/2010 | Milliman ............ A61B 17/1155 227/175.1 |

FOREIGN PATENT DOCUMENTS

| | | |
|---|---|---|
| EP | 643946 A2 | 3/1995 |
| EP | 656191 A2 | 6/1995 |
| EP | 820724 A2 | 1/1998 |
| EP | 820725 A2 | 1/1998 |
| EP | 885595 A1 | 12/1998 |
| EP | 1088519 A1 | 4/2001 |
| EP | 2030578 A1 | 3/2009 |
| FR | 1518083 A | 3/1968 |
| FR | 2777446 A1 | 10/1999 |
| GB | 935490 A | 8/1963 |
| WO | 8100668 A1 | 3/1981 |
| WO | 8801486 A1 | 3/1988 |
| WO | 9515715 A1 | 6/1995 |
| WO | 9517127 A1 | 6/1995 |
| WO | 9535065 A1 | 12/1995 |
| WO | 9740754 A1 | 11/1997 |
| WO | 9911178 A1 | 3/1999 |
| WO | 9917662 A1 | 4/1999 |
| WO | 9069343 A2 | 11/2000 |
| WO | 0152748 A2 | 7/2001 |
| WO | 0232323 A2 | 4/2002 |
| WO | 02058568 A1 | 8/2002 |
| WO | 03101314 A1 | 12/2003 |
| WO | 2004112583 A2 | 12/2004 |
| WO | 2008007377 A2 | 1/2008 |

* cited by examiner

SURGICAL FASTENING APPARATUS

CROSS-REFERENCE TO RELATED APPLICATIONS

This application is a continuation of U.S. patent application Ser. No. 13/787,368 filed Mar. 6, 2013, now U.S. Pat. No. 9,408,603, which is a continuation of U.S. patent application Ser. No. 12/899,617 filed Oct. 7, 2010, now U.S. Pat. No. 8,413,872, which claims benefit of and priority to U.S. Provisional Application No. 61/326,292 filed Apr. 21, 2010, which claims benefit of and priority to U.S. Provisional Application No. 61/255,529 filed Oct. 28, 2009, and the disclosures of each of the above-identified applications are hereby incorporated by reference in their entirety.

BACKGROUND

Technical Field

The present disclosure relates to a surgical fastening apparatus and, more particularly, to a surgical fastening apparatus having a fastener and retainer system.

Background of the Related Art

Various types of surgical stapling instruments for performing a circular anastomosis are well known, wherein an operator actuates the apparatus at a location which is relatively remote from the location at which the circular anastomosis takes place. Anastomosis is the surgical joining of separate hollow organ sections. Typically, an anastomosis procedure involves surgery in which a diseased or defective section of hollow tissue is removed.

A conventional surgical stapling instrument for performing a circular anastomosis in a hemorrhoidal or other surgical procedure generally includes a shell assembly having an annular array of staples and staple slots and an anvil assembly having a circular array of staple forming pockets in a proximal surface thereof. An example of surgical stapling instruments for performing circular anastomosis is described in U.S. Pat. Nos. 7,168,604, 7,303,106 and pending U.S. application Ser. No. 12/550,443, filed Aug. 31, 2009, all which are incorporated herein in their entirety by reference. Typically, the anvil assembly is longitudinally movable from an open position to a closed position which places the anvil assembly adjacent to the shell assembly to clamp the body tissue therebetween. After bringing the anvil and shell assemblies to a closed position to clamp tissue, an annular pusher including a plurality of pushers which are configured to eject a corresponding staple from the staple slot through the tissues and against a receiving pocket of the anvil to form staples is actuated by the operator in a relatively remote region to perform a circular anastomosis. After stapling the tissues together, the tissue is severed by the annular blade and extracted.

Surgical fastening instruments applying two part surgical fasteners are known. In these instruments, a plurality of retainers are supported in an anvil assembly and a plurality of fasteners are supported in a fastener holding assembly. The fasteners are advanced through tissue and into engagement with openings in respective retainers. These two part fasteners are typically composed of resorbable material. The firing force of the fasteners in some of these instruments could shift the retainers out of position which may result in misalignment. In addition, the retainers may slip against the anvil and/or may come off the anvil before firing which may also result in misalignment. Accordingly, it would be advantageous to provide a configuration which enhances mating of the fasteners and the retainers and it may be useful to provide such configuration in a circular anastomosis instrument.

SUMMARY

In accordance with the present disclosure, a surgical fastening apparatus includes in one aspect a fastener retaining frame which includes a first annular portion having a plurality of retainers disposed thereon and a second annular portion having a plurality of perforations formed therein. A fastener guide member contains a plurality of surgical fasteners mateable with the plurality of retainers to fasten tissue therebetween. The fastener retaining frame is detachably secured to a frame supporting structure. An annular pusher ejects the plurality of surgical fasteners from the fastener guide member towards the plurality of corresponding retainers. An annular blade severs the plurality of perforations after the plurality of surgical fasteners have been mated with the plurality of retainers.

In one embodiment, the surgical fastening apparatus further includes a flange member for detachably securing the fastener retaining frame, wherein the flange member is fixedly attached to an anvil. The second annular portion defining the plurality of perforations may be concentrically arranged within the first annular portion having the plurality of retainers circumferentially disposed thereon. In an embodiment, the first annular portion has a plurality of links connecting the plurality of retainers circumferentially disposed thereon forming a single body of retainers. In an alternative embodiment, the plurality of retainers are monolithically formed. In one embodiment, the first annular portion is monolithically formed with the second annular portion. The plurality of retainers circumferentially disposed on the first annular portion of the fastener retaining frame may be arranged to define two concentric rings of retainers.

In one embodiment, the plurality of retainers are substantially uniformly spaced apart. In another embodiment, the plurality of circumferentially disposed perforations on the second annular portion are substantially uniformly spaced apart. The retainers may be made of biodegradable polymer. The plurality of surgical fasteners may also be made of biodegradable polymer. The fastener retaining frame may be made of biodegradable polymer.

In one embodiment, the flange member defines an annular recess to dispose therein the fastener retaining frame, wherein the flange member can include a ledge to securely dispose the fastener retaining frame in the annular recess thereof. A distal side of the fastener retaining frame may be axially tapered with respect to the thickness thereof. The annular recess defined by flange member may also be axially tapered with respect to the thickness thereof corresponding to the axially tapered fastener retaining frame. The fastener retaining frame in some embodiments has a snap-fit configuration with the flange member.

In one embodiment, each of the plurality of perforations defined in the second annular portion has a radially notched portion configured to facilitate breaking off thereof upon actuation of the annular blade. In another embodiment, each of the plurality of perforations defined in the second annular portion has a pair of opposing slits configured to facilitate breaking off thereof upon actuation of the annular blade. In one embodiment, the plurality of surgical fasteners are configured to snap-fit with the plurality of retainers. In some embodiments, the thickness of a part defining the plurality of perforations in the second annular portion of the fastener retaining frame is less than that of the rest of the second annular portion to facilitate breaking off of the plurality of perforations. In some embodiments, the fastener retaining frame may be elastic. In some embodiments, the fastener guide member may include a plurality of fastener slots axially extending and circumferentially arranged for accommodating therein the plurality of surgical fasteners.

BRIEF DESCRIPTION OF THE DRAWINGS

The above and other objects and features of the present disclosure will become apparent from the following description of embodiments given in conjunction with the accompanying drawings, in which.

DETAILED DESCRIPTION OF THE EMBODIMENTS

Figure 1:
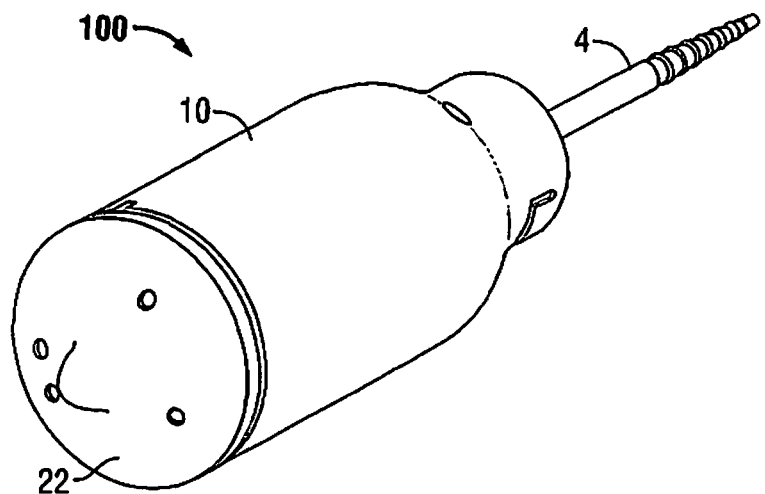
FIG. 1 is a front perspective view of an end effector in accordance with an embodiment of the present disclosure.

Various embodiments of the presently disclosed end effector will now be described in detail with reference to the drawings, wherein like references numerals identify similar or identical elements. In the drawings and in the description which follows, the term "proximal" will refer to the end of the component that is closer to the operator during use, while the term "distal" will refer to the end of the component that is farther from the operator, as is traditional and conventional in the art.

Figure 2:
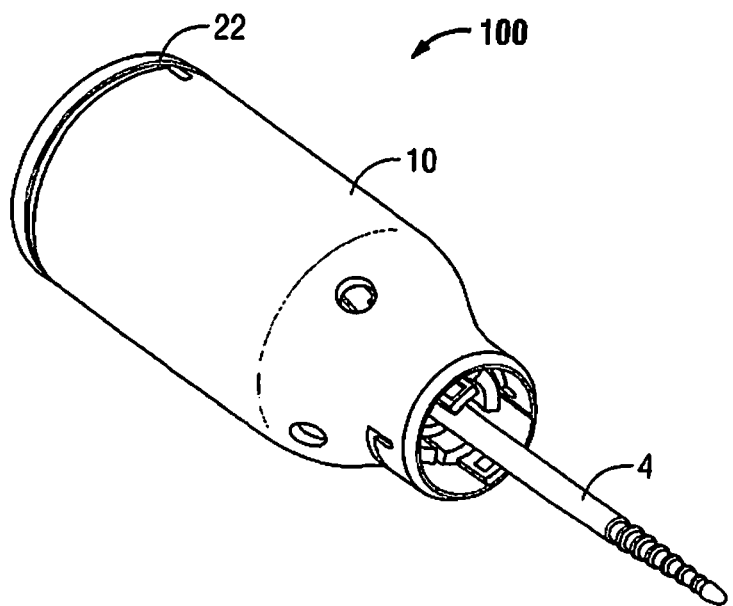
FIG. 2 is a rear perspective view of the end effector of FIG. 1.
Figure 7:
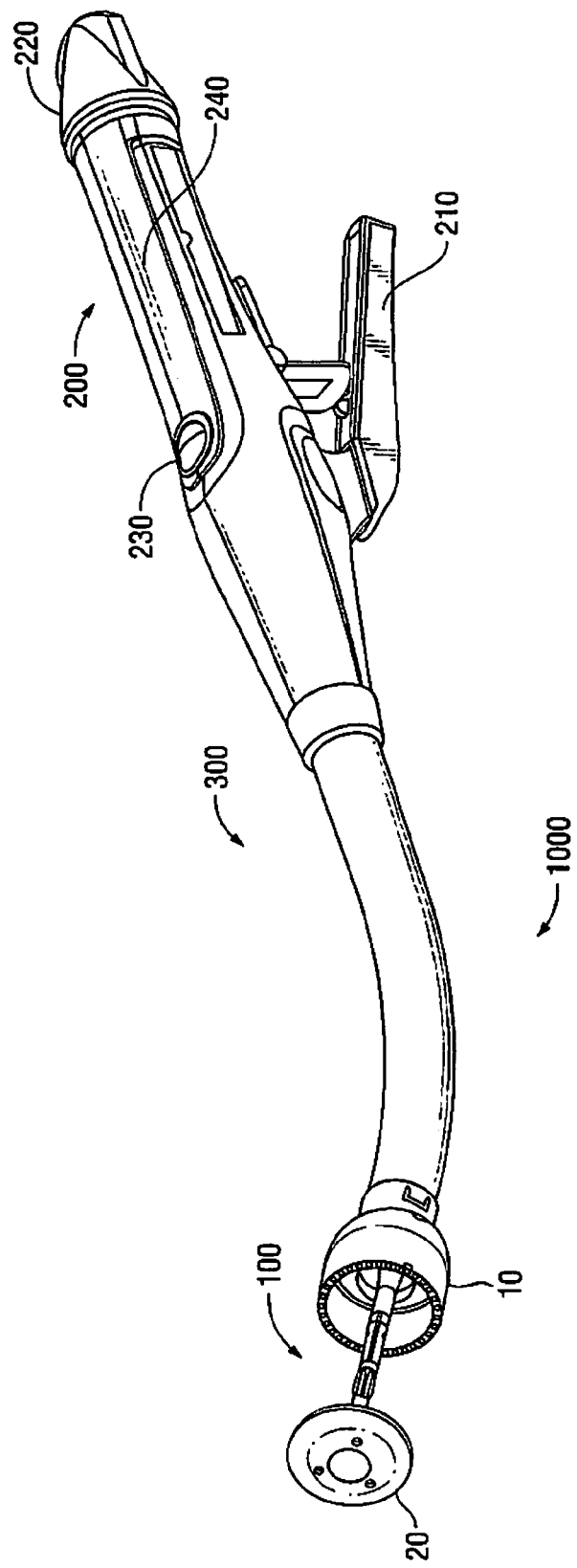
FIG. 7 is a perspective view of a surgical fastening apparatus including the end effector of FIG. 1 in accordance with an embodiment of the present disclosure.

With reference to FIGS. 1, 2 and 7, an end effector 100 suitable for a surgical fastening apparatus 1000 is illustrated. A suitable example of a surgical fastening apparatus 1000 is disclosed in U.S. Pat. Nos. 7,168,604, 7,303,106 and U.S. application Ser. No. 12/550,443, filed Aug. 31, 2009. The entire contents of each of these patents/application are incorporated by reference herein. The surgical fastening apparatus 1000 includes a handle assembly 200, an elongate shaft 300 extending distally therefrom, and an end effector 100 coupled to the distal end of the elongate shaft 300. The length and the curvature of elongate shaft 300 may be tailored to meet the specific needs of surgical procedure being performed. Elongate shaft 300 alternatively may be flexible to facilitate maneuvering of surgical fastening apparatus 1000, more specifically, end effector 100, to the targeted area in the body containing tissues to be joined.

The handle assembly 200 generally includes a stationary handle 240, a pivotable trigger 210 and a rotatable knob 220. When rotatable knob 220 is manually rotated, anvil assembly 20 will longitudinally translate in relation to shell assembly 10 between an open position and a closed position in a manner to be described below. Actuation of trigger 210 towards stationary handle 240 advances annular pusher 40 (FIG. 3) distally within shell assembly 10 to eject fasteners from shell assembly 10 in a manner described below. Actuation of trigger 210 also longitudinally translates a circular knife 51 that severs tissue as well as separates the formed fasteners from a retaining frame in a manner described below.

Figure 3:
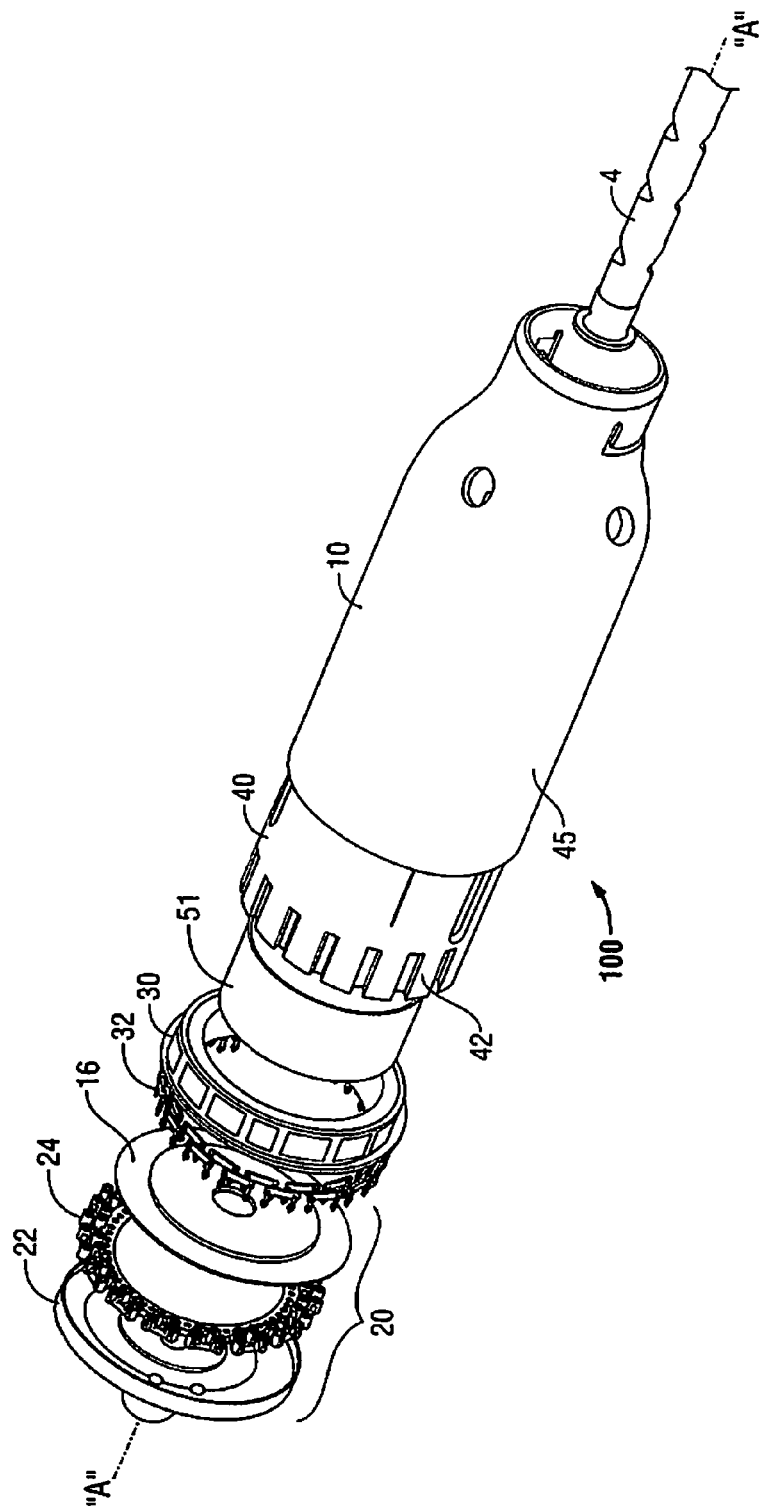
FIG. 3 is an exploded perspective view of the end effector shown in FIG. 1.
Figure 5:
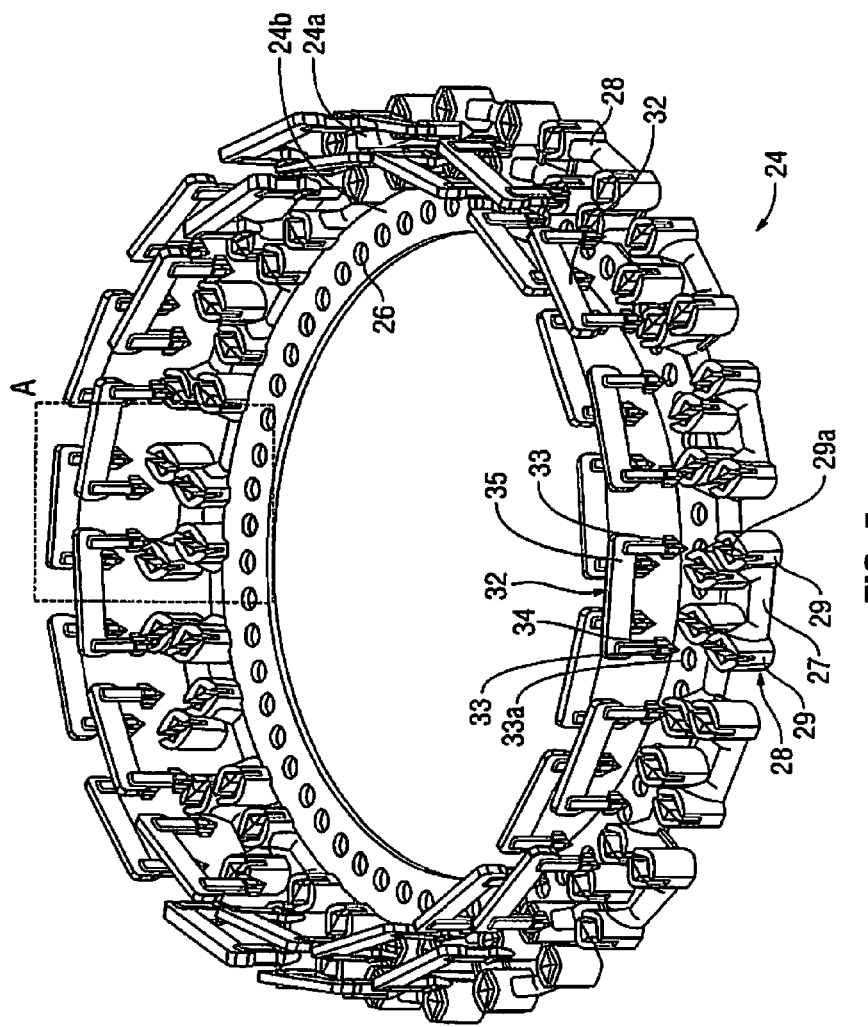
FIG. 5 is a perspective view of a fastener retaining frame and a plurality of fasteners prior to engagement.

Referring now to FIGS. 3, and 5 an embodiment of the present disclosure is shown generally as staple end effector 100 defining a longitudinal axis "A-A." Staple end effector 100 includes an anvil assembly 20 and a shell assembly 10. Anvil assembly 20 includes an anvil 22, fastener retaining frame 24, and a flange member 16. Flange member 16 is preferably composed of plastic material such as HDPE. As will be discussed in further detail below, fastener retaining frame 24 includes a plurality of perforations 26 and a plurality of retainers 28 (FIG. 5) and is detachably secured to flange member 16 which is fixedly attached to anvil 22. Shell assembly 10 accommodates therein a fastener guide member 30 which includes a plurality of axially extending and circumferentially arranged fastener slots 34 for receiving therein a plurality of axially extending surgical fasteners 32 having distally directed tissue piercing prongs for mating with the plurality of retainers 28 on fastener retaining frame 24 to fasten tissue therebetween. Shell assembly 10 further accommodates therein an annular pusher 40 including a plurality of pusher fingers 42 operably associated with the plurality of surgical fasteners 32. Each pusher 42 is configured for ejecting an associated surgical fastener 32 towards a corresponding retainer 28 on fastener retaining frame 24. A distal end of drive shaft 4 is operably connected with annular pusher 40 and a proximal end of drive shaft 4 is operably connected with trigger 210, whereby the actuation of trigger 210 distally advances drive shaft 4 which advances annular pusher 40 within housing 45 of shell assembly 10 to eject surgical fasteners 32 from fastener guide member 30 in a manner to be described below. A circular knife 51 with an annular cutting blade is advanced by pusher 40 to sever tissue in the manner described below.

Figure 6:
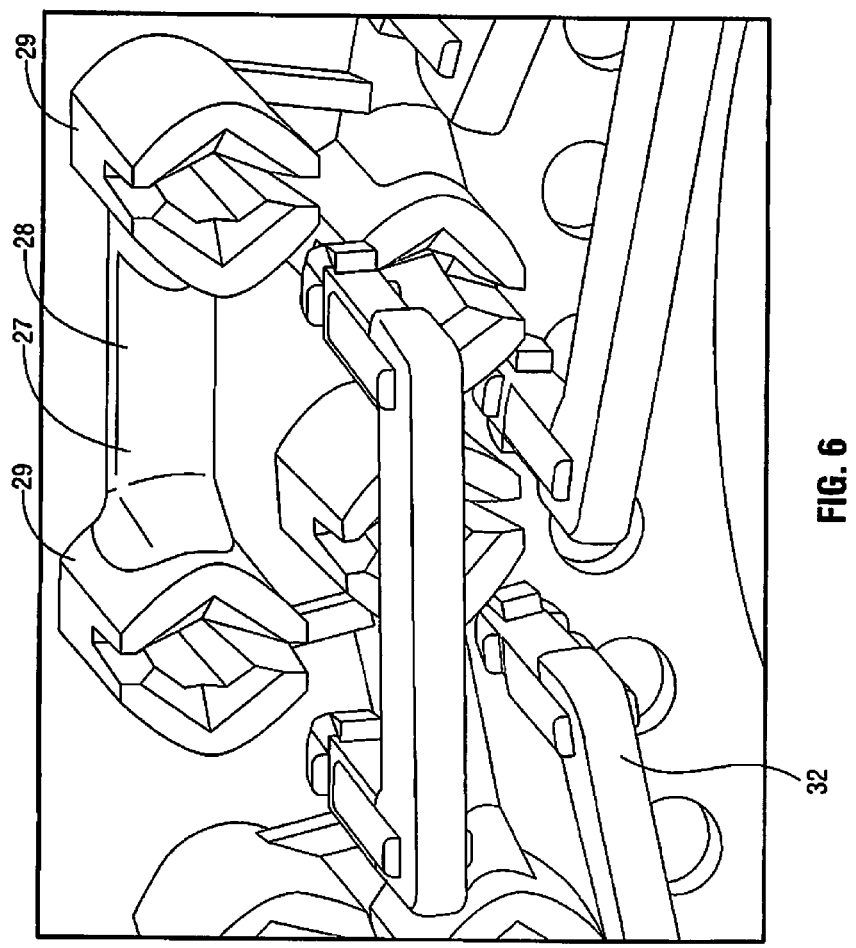
FIG. 6 is an enlarged view of detail area "A" of FIG. 5.

With particular reference to FIGS. 5 and 6, fastener retaining frame 24 will be described in detail. Fastener retaining frame 24 includes a first annular portion 24a having a plurality of retainers 28 circumferentially disposed thereon and a second annular portion 24b having a plurality of circumferentially arranged perforations 26. The two annular portions 24a and 24b are concentrically arranged, with the second annular portion 24b concentrically arranged within (radially inward of) the first annular portion 24a. The plurality of retainers 28 are either monolithically formed or are individually formed and connected by suitable structures, e.g., links, thereby forming a single body. Moreover, first annular portion 24a may be monolithically formed with second annular portion 24b. The first annular portion 24a and the second annular portion 24b may be made of different materials; in some embodiments they are made of biodegradable polymers (e.g. L4). For clarity, only a few of the retainers, perforations, etc. are labeled.

With reference still to FIGS. 5, and 6 each retainer 28 includes a bridge 27 and a pair of posts 29 each forming a cavity or opening 29a therein (note for clarity only one of the retainers is labeled in FIG. 5). Each retainer 28 is mated with an associated surgical fastener 32. Specifically, each prong 33 of the associated surgical fastener 32 is inserted into each cavity 29a of an associated retainer 28. Surgical fastener 32 and retainer 28 may be configured to engage in a snap-fit manner. Furthermore, a tip 33a of each prong 33 may include a barb 34 to enhance secure mating with retainer 28. Bridge or backspan 35 extends between prongs 33. The plurality of retainers 28 circumferentially disposed on first annular portion 24a of fastener retaining frame 24 are arranged to define a ring of retainers 28. The first annular portion 24a in the illustrated embodiment includes two rings of retainers 28 wherein each ring has 16 retainers, although a different number of retainers and/or a different number of rings is contemplated. When more than one ring of retainers 29 is present in first annular portion 24a, retainers 28 forming one ring may be radially aligned with those forming another ring. Alternatively, retainers 28 forming one ring may have a partial overlap or be radially offset with those forming another ring as to allow uniform integrity of circular stapling. Retainers 28 may be substantially uniformly spaced apart; however, the spacing between retainers 28 may be tailored to meet the specific needs of the surgical operation being performed. The fasteners 32 and retainers 28 are preferably made of a resorbable material.

With reference still to FIG. 5, fastener retaining frame 24 includes a plurality of perforations 26 in second annular portion 24b thereof. The plurality of perforations 26 may be substantially uniformly formed (substantially uniformly spaced apart) in second annular portion 24b. As an alternative to equidistant spacing or substantially equidistant spacing, other spacings for the perforations are also contemplated including perforations arbitrarily defined or otherwise spaced. In one embodiment, the plurality of perforations 26, like retainers 28, may define more than one ring of perforations. The diameter of each of the plurality of perforations 26 may be selected such that the thickness of the annular blade is less than the diameter of each of the perforations 26. Such configuration may facilitate severing or breaking off of the plurality of perforations 26. In addition, each perforation 26 may include a radially notched portion configured to facilitate severing or breaking off of perforations 26 upon actuation of annular pusher 40. Alternatively, each perforation 26 may include a pair of opposing slits also serving to facilitate breaking off of perforations 26 upon actuation of annular pusher 40. When employing perforations 26 containing for example the pair of slits, the width of the slits may be chosen to correspond with the thickness of the annular blade to allow the annular blade to be engaged within the opposing slits of the associated perforation. In some embodiments, the thickness of second annular portion 24b defining the plurality of perforations 26 may be varied. For example, an inner part of the second annular portion 24b, i.e., a part that is inside of the plurality of perforations 26, can have a thickness less than that of an outer part of second annular portion 24b, i.e., a part that is in contact with first annular portion 24a, whereby the relatively thinner part or a more brittle part can have to facilitate breaking off of perforations 26 resulting in a detachment of fastener retaining frame 24 from flange member 16 as will be discussed below. In the alternative, the thickness of only a part defining the plurality of perforations 26 may be less than that of the rest of second annular portion 24b whereby such configuration also facilitates breaking off of the plurality of perforations 26 resulting in a detachment of fastener retaining frame 24 from flange member 16.

Figure 4:
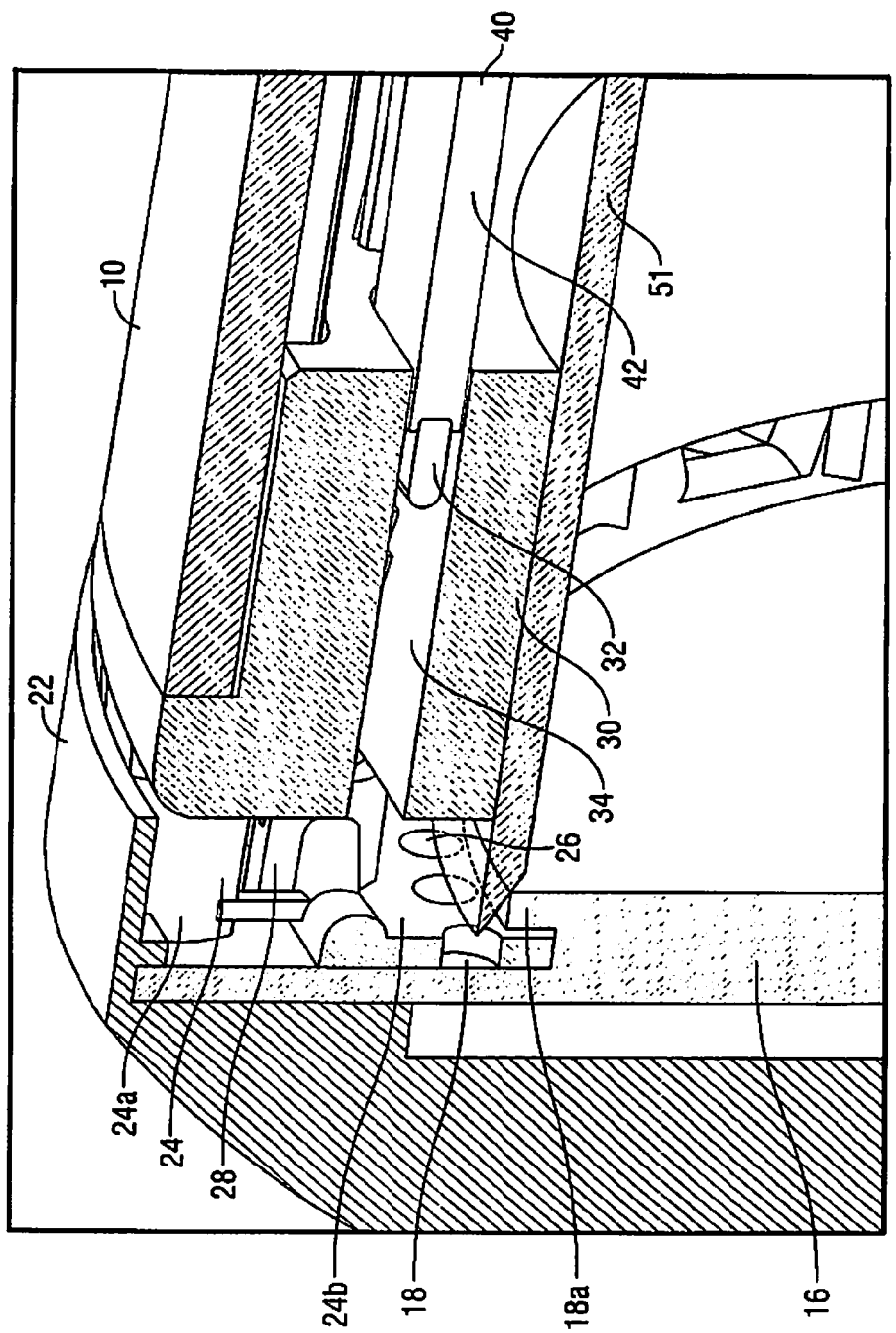
FIG. 4 is a partial cross-sectional perspective view of the distal end of the end effector of FIG. 1.

Turning back to FIG. 4, anvil assembly 20 in a closed position prior to the firing of surgical fasteners 32 by the actuation of trigger 210 is illustrated. Flange member 16 has an annular recess 18 and includes a ledge 18a to form a supporting/retaining structure for the fastener retaining frame 24. Fastener retaining frame 24 is disposed in annular recess 18 and is secured therein by ledge 18a. FIG. 4 illustrates ledge 18a securing fastener retaining frame 24 at second annular portion 24b. Accordingly, the thickness of the inner part of second annular portion 24b and/or the rigidity of second annular portion 24b may be chosen, e.g., by choosing the material having the requisite rigidity, to prevent bending of the mated fastener retaining frame 24 at perforations 26 and/or at a location in contact with ledge 18a prior to severing the plurality of perforations 26. In one embodiment, a distal side of fastener retaining frame 24 is axially tapered with respect to the thickness thereof to enhance secure attachment thereof to annular recess 18 of flange member 16 also axially tapered with respect to the thickness thereof. Flange member 16 having fastener retaining frame 24 detachably secured thereto is fixedly attached to anvil 22 so that fastener retaining frame 24 and anvil 22 move as a single unit in an longitudinal translation thereof through a manual operation of the rotational knob 220 by the operator.

Still referring to FIG. 4, shell assembly 10 accommodates fastener guide member 30 which contains a plurality of circumferentially arranged and axially extending fastener slots 34 for receiving therein a plurality of axially extending surgical fasteners 32 having tissue piercing prongs 33 for mating with plurality of retainers 28 on fastener retaining frame 24 to fasten body tissue therebetween. FIG. 4 illustrates a surgical fastener 32 loaded in fastener slot 34 and having a proximal side thereof engaged with an associated pusher 42 prior to being fired.

In use, anvil assembly 20 is spaced from shell assembly 10 as shown in FIG. 7 such that the end effector is an open or unapproximated position. Once the body tissues to be fastened are placed in the open space between anvil assembly 20 and shell assembly 10, anvil assembly 20 is translated proximally to an approximated position to clamp the body tissues therebetween such that the end effector is in a closed or approximated position. This is achieved by rotating the rotatable knob 220 of the handle assembly 200.

As shown in FIG. 4, anvil assembly 20 in a pre-fired closed position is engaged with shell assembly 10 (see also FIG. 1).

The attachment of fastener retaining frame 24 to flange member 16, which is fixedly attached to anvil 22, reduces slippage of fastener retaining frame 24 against anvil 22 and retains its position with respect to anvil 22 during axial translations thereof. Once the clamping of the body tissues has taken place, the operator actuates trigger 210 which in turn distally drives the drive shaft 4 connected to annular pusher 40. The plurality of pushers 42 on the distally translated annular pusher 40 ejects the corresponding set of surgical fasteners 32 from fastener slots 34 of fastener guide member 30. Each of the ejected set of surgical fasteners 32 pierce through the body tissue and are received into a corresponding retainer 28. Specifically, a portion of each of the prongs of fasteners 32 is received into a respective cavity 29a formed in posts 29 in retainer 28. Note the tip 33 and barbs 34 of fastener prongs 33 deform receiving walls 29b of posts 29 as the fastener prong 33 is forced through cavity 29a. The barbs engage a ledge of the cavity 29a to prevent retraction (proximal movement) of the fastener 32, thereby locking the fastener 32 with the respective retainer 28. Note that since fastener retaining frame 24 is securely attached to flange member 16 which is fixedly attached to anvil 22, slippage of fastener retaining frame 24 against anvil 22 due to the firing force produced by the actuation of trigger 210 which ejects the plurality of fasteners 32 from fastener slots 34 into the body tissues is reduced. Thus, the position of fastener retaining frame 24 is maintained with respect to anvil 22 during the firing of surgical fasteners 32. Moreover, the plurality of retainers 28 are either monolithically formed or individually formed and connected by suitable structures, e.g., links, thereby forming a single body. In either instance, the configuration of the plurality of retainers 28 as a single body, in conjunction with fastener retaining frame 24 being secured to flange member 16 which is fixedly attached to anvil 22, reduces the radial misalignment of surgical fasteners 32 with fastener retaining frame 24.

As noted above, fastener retaining frame 24 and fastener guide member 30 may be configured to provide a plurality of rings of surgical fasteners 32 on tissues, e.g., two rings of surgical fasteners wherein each ring is defined by sixteen fasteners, to meet the needs of the specific procedure being performed. Upon mating of the plurality of surgical fasteners 32 with fastener retaining frame 24, an annular blade 51 is actuated to distally translate through shell assembly 10. Note the annular blade can be translatable by actuation of the trigger 210 which advances the fasteners, or alternatively by a separate actuator actuated in a separate step. The annular blade comes into contact with fastener retaining frame 24 and is pressed against the plurality of perforations 26 defined in the fastener retaining frame 24 severing or breaking perforations 26. The broken or severed perforations 26 enable the mated surgical fastener 32 and fastener retaining frame 24 to be detached from anvil 22. The severing or breaking off of perforations 26 leaves a residuary ring, i.e., the inner part of second annular portion 24b of fastener retaining frame 24, within ledge 18a of annular recess 18 of flange member 16. In some embodiments, in order to prevent perforation chips that may be produced during the severing or breaking off of perforations 26, each of the plurality of perforations 26 may be provided with, for example, a pair of opposing slits or a notched portion, as mentioned above, wherein the thickness of the annular blade is chosen to be smaller than, e.g., the width of the pair of opposing slits. The mated surgical fastener 32 and fastener retaining frame 24 fastening body tissue therebetween would then be free to displace without being restricted or attached to anvil 22. Actuation of the knife severs the tissue. The operator then moves anvil 22 to the open (unapproximated) position by rotating the rotatable knob 220 of the handle assembly thereby distally translating anvil assembly 20. After the removal of the severed tissue, e.g. hemorrhoidal tissue, the surgical fastening device is removed from the body.

From the foregoing and with reference to the various figure drawings, those skilled in the art will appreciate that certain modifications can also be made to the present disclosure without departing from the scope of the same. For example, the annular blade may be fixedly secured to the anvil and configured to break the plurality of perforations on the fastener retaining frame upon firing of the plurality of fasteners. Such design eliminates the need for a longitudinal translation of the annular blade. Additionally, although disclosed as annular portions for use with a circular fastening apparatus, use of linear portions for use with apparatus applying linear arrays of fasteners are also contemplated.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector of a surgical instrument comprising:
    a tubular body including a plurality of surgical fasteners therein;
    an anvil movable relative to the tubular body between open and approximated positions;
    a fastener retaining frame including a plurality of retainers configured to mate with the plurality of surgical fasteners; and
    a flange secured with the anvil, the flange defining a recess configured to receive a portion of the fastener retaining frame therein, the flange including a ledge in registration with a part of the fastener retaining frame to secure the portion of the fastener retaining frame in the recess of the flange, wherein the portion of the fastener retaining frame is severable, whereby the plurality of the retainers is detachable from the anvil.

2. The end effector of the surgical instrument according to claim 1, wherein the plurality of retainers is circumferentially arranged on the fastener retaining frame.

3. The end effector of the surgical instrument according to claim 1, wherein the ledge of the flange extends radially over the portion of the fastener retaining frame to secure the portion of the fastener retaining frame within the recess of the flange, such that when the portion of the fastener retaining frame is severed from the plurality of retainers, the part of the fastener retaining frame is retained within the recess of the flange.

4. The end effector of the surgical instrument according to claim 1, wherein the portion of the fastener retaining frame includes a weakened portion.

5. The end effector of the surgical instrument according to claim 4, wherein the weakened portion is circumferentially arranged on the fastener retaining frame.

6. The end effector of the surgical instrument according to claim 4, wherein the weakened portion of the fastener retaining frame defines a plurality of perforations.

7. The end effector of the surgical instrument according to claim 1, wherein the fastener retaining frame includes a first annular portion including the portion of the fastener retaining frame received in the recess of the flange.

8. The end effector of the surgical instrument according to claim 7, wherein the fastener retaining frame further includes a second annular portion including the plurality of retainers.

9. The end effector of the surgical instrument according to claim 8, wherein the second annular portion is disposed about the first annular portion.

10. The end effector of the surgical instrument according to claim 8, wherein at least one of the first or second annular portions is made of biodegradable polymers.

11. The end effector of the surgical instrument according to claim 1, wherein the plurality of retainers is monolithically formed.

12. The end effector of the surgical instrument according to claim 1, wherein the plurality of retainers is arranged to define two concentric rings of retainers.

13. The end effector of the surgical instrument according to claim 12, wherein the two concentric rings of retainers are radially offset from each other.

14. The end effector of the surgical instrument according to claim 1, wherein each retainer of the plurality of retainers defines a pair of cavities configured to receive prongs of the respective surgical fasteners.

15. The end effector of the surgical instrument according to claim 1, wherein the tubular body further includes an annular pusher for ejecting the plurality of surgical fasteners toward the respective retainers.

16. The end effector of the surgical instrument according to claim 1, wherein the tubular body further includes an annular blade for severing the portion of the fastener retaining frame to detach the plurality of retainers from the anvil.

17. The end effector of the surgical instrument according to claim 16, wherein a thickness of the annular blade of the tubular body is less than a diameter of each perforation of a plurality of perforations defined in the portion of the fastener retaining frame.

18. The end effector of the surgical instrument according to claim 1, wherein the fastener retaining frame is detachably secured to the flange.

19. An end effector of a surgical instrument comprising:
a tubular body including a plurality of surgical fasteners therein;
an anvil movable relative to the tubular body to clamp tissue therebetween;
a fastener retaining frame including a plurality of retainers configured to mate with the plurality of surgical fasteners of the tubular body; and
a flange secured with the anvil, the flange defining a recess configured to receive a portion of the fastener retaining frame therein, the flange including a ledge extending radially over the portion of the fastener retaining frame to secure the portion of the fastener retaining frame within the recess of the flange, wherein the portion of the fastener retaining frame is severable, such that the plurality of the retainers is detachable from the anvil.

20. The end effector of the surgical instrument according to claim 19, wherein the plurality of retainers is circumferentially arranged about the recess of the flange.

21. The end effector of the surgical instrument according to claim 19, wherein when the portion of the fastener retaining frame is severed from the plurality of retainers, a part of the fastener retaining frame is retained within the recess of the flange.

22. The end effector of the surgical instrument according to claim 19, wherein the plurality of retainers is arranged circumferentially on the fastener retaining frame to define two concentric rings of retainers.

23. The end effector of the surgical instrument according to claim 19, wherein the tubular body further includes an annular blade for severing the portion of the fastener retaining frame to detach the plurality of retainers from the anvil.

* * * * *